US006316095B1

(12) United States Patent
Black et al.

(10) Patent No.: US 6,316,095 B1
(45) Date of Patent: Nov. 13, 2001

(54) 2-OXETANONE SIZING AGENTS AND THEIR USE IN PAPER

(75) Inventors: Donald K. Black; Kyle J. Bottorff, both of Newark, DE (US); Clement Linus Brungardt, Oxford, PA (US); David Howard Dumas, Wilmington, DE (US); Susan Merrick Ehrhardt, Haddonfield, NJ (US); John Charles Gast, Hockessin; Jian-Jian Zhang, Wilmington, both of DE (US)

(73) Assignee: Hercules Incorporated, Wilmington, DE (US)

( * ) Notice: Subject to any disclaimer, the term of this patent is extended or adjusted under 35 U.S.C. 154(b) by 0 days.

(21) Appl. No.: 09/420,040

(22) Filed: Oct. 18, 1999

Related U.S. Application Data

(60) Continuation of application No. 09/244,108, filed on Feb. 4, 1999, now Pat. No. 6,244,373, which is a division of application No. 08/911,121, filed on Aug. 14, 1997, now Pat. No. 6,007,906, which is a division of application No. 08/428,288, filed on Apr. 25, 1995, now Pat. No. 5,879,814, which is a continuation of application No. 08/192,570, filed on Feb. 7, 1994, now Pat. No. 5,685,815.

(51) Int. Cl.[7] .................................................. C07D 305/12

(52) U.S. Cl. ....................... 428/323; 428/537.5; 549/328; 549/329; 549/510

(58) Field of Search ................................ 428/323, 537.5, 428/402; 549/328, 329, 510

(56) References Cited

U.S. PATENT DOCUMENTS

| | | | | |
|---|---|---|---|---|
| 4,522,686 | * | 6/1985 | Dumas | 162/158 |
| 5,466,708 | * | 11/1995 | Derungs et al. | 514/449 |
| 5,685,815 | * | 11/1997 | Bottorff et al. | 493/186 |
| 5,725,731 | * | 3/1998 | Brungardt et al. | 162/72 |
| 5,879,814 | * | 3/1999 | Bottorff | 428/537.5 |
| 5,889,814 | * | 3/1999 | Bottorff | 428/537.5 |
| 6,007,906 | * | 12/1999 | Bottorff et al. | 428/323 |
| 6,048,392 | * | 4/2000 | Brungardt et al. | 106/287.21 |
| 6,197,417 | * | 3/2001 | Bottorff | 428/323 |

* cited by examiner

*Primary Examiner*—Hoa T. Le
(74) *Attorney, Agent, or Firm*—Gary A. Samuels; Mark D. Kuller

(57) ABSTRACT

Fine paper that is sized with a 2-oxetanone alkaline sizing agent and that does not encounter machine feed problems in high speed converting or reprographic machines, including continuous forms bond paper and adding machine paper, processes for converting the paper into envelopes, continuous forms bond paper and adding machine paper, and paper products of the processes.

31 Claims, No Drawings

2-OXETANONE SIZING AGENTS AND THEIR USE IN PAPER

This application is a divisional of U.S. patent application Ser. No. 08/911,121, filed Aug. 14, 1997, now U.S. Pat. No. 6,007,906 which is a continuation of U.S. patent application Ser. No. 08/192,570, filed Feb. 7, 1994, now U.S. Pat. No. 5,685,815 and a divisional of U.S. patent application Ser. No. 08/428,288, filed Apr. 25, 1995, now U.S. Pat. No. 5,879,814 (which is a division of U.S. patent application Ser. No. 08/192,570, now U.S. Pat. No. 5,685,815), all of which are incorporated herein in their entirety by reference. In addition, this application is a continuation of U.S. patent application Ser. No. 09/244,108, filed Feb. 4, 1994, now U.S. Pat. No. 6,244,373 which is also incorporated in its entirety by reference, and which is a continuation of U.S. patent application Ser. No. 08/428,288 now U.S. Pat. No. 5,879,814.

This invention relates to paper containing alkaline sizing agents for paper that have a reactive functional group that covalently bonds to cellulose fiber and hydrophobic tails that are oriented away from the fiber, and processes for using the paper.

BACKGROUND OF THE INVENTION

The amount of fine paper produced under alkaline conditions has been increasing rapidly, encouraged by cost savings, the ability to use precipitated calcium carbonate (PCC), an increased demand for improved paper permanence and brightness, and an increased tendency to close the wet-end of the paper machine.

Current applications for fine paper require particular attention to sizing before conversion or end-use, such as high-speed photocopies, envelopes, forms bond including computer printer paper, and adding machine paper. The most common sizing agents for fine paper made under alkaline conditions are alkenyl succinic anhydride (ASA) and alkyl ketene dimer (AKD). Both types of sizing agents have a reactive functional group that covalently bonds to cellulose fiber and hydrophobic tails that are oriented away from the fiber. The nature and orientation of these hydrophobic tails cause the fiber to repel water.

Commercial AKD's, containing one β-lactone ring, are prepared by the dimerization of the alkyl ketenes made from two saturated, straight-chain fatty acid chlorides; the most widely used being prepared from palmitic and/or stearic acid. Other ketene dimers, such as the alkenyl based ketene dimer (Aquapel® 421 of Hercules Incorporated), have also been used commercially. Ketene multimers, containing more than one such β-lactone ring, have been described in Japanese Kokai 168992/89, the disclosure of which is incorporated herein by reference. ASA-based sizing agents may be prepared by the reaction of maleic anhydride with an olefin ($C_{14}$–$C_{18}$).

Although ASA and AKD sizing agents are commercially successful, they have disadvantages. Both types of sizing agents, particularly the AKD type, have been associated with handling problems in the typical high-speed conversion operations required for the current uses of fine paper made under alkaline conditions (referred to as alkaline fine paper). The problems include reduced operating speed in forms presses and other converting machines, double feeds or jams in high-speed copiers, and paper-welding and registration errors on printing and envelope-folding equipment that operates at high speeds.

These problems are not normally associated with fine paper produced under acid conditions (acid fine paper). The types of filler and filler addition levels used to make alkaline fine paper differ significantly from those used to make acid fine paper, and can cause difference in paper properties such as stiffness and coefficient of friction which affect paper handling. Alum addition levels in alkaline fine paper, which contribute to sheet conductivity and dissipation of static, also differ significantly from those used in acid fine paper. This is important because the electrical properties of paper affect its handling performance. Sodium chloride is often added to the surface of alkaline fine paper to improve its performance in end use.

The typical problems encountered with the conversion and end-use handling of alkaline fine paper involve:

1. Paper properties related to composition of the furnish;
2. Paper properties developed during paper formation; and
3. Problems related to sizing.

The paper properties affected by paper making under alkaline conditions that can affect converting and end-use performance include:

Curl
Variation In Coefficient of Friction
Moisture Content
Moisture Profile
Stiffness
Dimensional Stability
MD/CD Strength Ratios One such problem has been identified and measured as described in "Improving The Performance Of Alkaline Fine Paper On The IBM 3800 Laser Printer," TAPPI Paper Makers Conference Proceedings (1991), the disclosure of which is incorporated herein by reference. The problem occurs when using an IBM 3800 high speed continuous forms laser printer that does not have special modifications intended to facilitate handling of alkaline fine paper. That commercially-significant laser printer therefore can serve as an effective testing device for defining the convertibility of various types of sized paper on state-of-the-art converting equipment and its subsequent end-use performance. In particular, the phenomenon of "billowing" gives a measurable indication of the extent of slippage on the IBM 3800 printer between the undriven roll beyond the fuser and the driven roll above the stacker.

Such billowing involves a divergence of the paper path from the straight line between the rolls, which is two inches above the base plate, causing registration errors and dropped folds in the stacker. The rate of billowing during steady-state running time is measured as the billowing height in inches above the straight paper path after 600 seconds of running time and multiplied by 10,000.

Typical alkaline AKD sized fine paper using a size furnish of 2.2 lbs. per ton of paper shows an unacceptable rate-of-billowing, typically of the order of 20 to 80. Paper handling rates on other high-speed converting machinery, such as a Hamilton-Stevens continuous forms press or a Winkler & Dunnebier CH envelope folder, also provide numerical measures of convertibility.

There is a need for alkaline fine paper that provides improved handling performance in typical converting and reprographic operations. At the same time, the levels of sizing development need to be comparable to that obtained with the current furnish levels of AKD or ASA for alkaline fine paper.

SUMMARY OF THE INVENTION

The invention comprises paper made under alkaline conditions and treated with a 2-oxetanone-based sizing agent (herein referred to as 2-oxetanone sizing agent), that at 35° C. is not a solid (not substantially crystalline, semi-crystalline, or waxy solid; i.e., it flows on heating without heat of fusion).

More preferably, the sizing agent according to the invention is a liquid at 25° C., or even at 20° C. (The references to "liquid" of course apply to the sizing agent per se and not to an emulsion or other combination.) The paper according to the invention does not encounter significant machine-feed problems on high speed converting machines and reprographic operations. Such problems are defined as significant in any specific conversion or reprographic application if they cause misfeeds, poor registration, or jams to a commercially unacceptable degree as will be discussed below, or cause machine speed to be reduced.

The preferred structure of 2-oxetanone sizing agents is as follows:

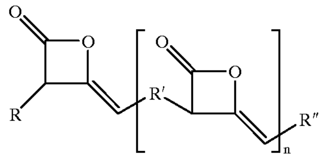

in which n can be 0 to 6, more preferably 0 to 3, and most preferably 0, and R and R", which may be the same or different, are selected from the group of straight or branched alkyl or alkenyl chains, provided that not all are straight alkyl chains and preferably at least 25% by weight of the sizing agent consists of the 2-oxetanone structure in which at least one of R and R" is not straight chain alkyl.

R and R" are substantially hydrophobic in nature, are acyclic, and are at least 6-carbon atoms in length. When n>0 the materials are termed 2-oxetanone multimers.

R' is preferably straight chain alkyl, more preferably $C_6$–$C_{16}$ straight chain alkyl, most preferably $C_{8-12}$ straight chain alkyl.

Preferably the invention further comprises alkaline paper that is treated with the 2-oxetanone based sizing agent according to the invention and contains a water soluble inorganic salt of an alkali metal, preferably NaCl, as well as alum and precipitated calcium carbonate (PCC). However, the paper of this invention will often be made without NaCl.

The paper of this invention is generally sized at a size addition rate of at least 0.5, preferably at least about 1.5, and most preferably at least 2.2 pounds/ton or higher. It may be, for instance, continuous forms bond paper, adding machine paper, or envelope-making paper, as well as the converted products, such as copy paper envelopes.

Also, the invention preferably comprises paper that is made under alkaline papermaking conditions and sized with a 2-oxetanone-based sizing agent having irregularities in the chemical structure of its pendant hydrophobic constituents; i.e., the said chemical structure contains irregularities such as carbon-to-carbon double bonds or branching in one or more of the hydrocarbon chains. (Conventional AKD'S are regular in that they have saturated straight-chain hydrocarbon chains).

Preferably according to the invention, paper that is made under alkaline papermaking conditions is sized with a sizing agent containing the 2-oxetanone functionality. Preferably the 2-oxetanone sizing agent is made from a fatty acid selected from the group consisting of oleic, linoleic, linolenic or palmitoleic fatty acid chlorides, or a mixture of them. More preferably, the 2-oxetanone sizing agent made from a fatty acid selected from the said group is at least 25% of the sizing agent, more preferably at least about 50% and most preferably at least about 70%. Also preferably each pendant hydrocarbon chain has 6 to 22 carbon atoms, most preferably 10 to 22 carbon atoms.

Preferably the paper according to the invention is capable of performing effectively in tests that measure its convertibility on state-of-the-art converting equipment and its performance on high speed end-use machinery. In particular, the paper according to the invention, that can be made into a roll of continuous forms bond paper having a basis weight of from about 30 to 60 lbs./3000 $ft^2$, more specifically about 40 to 50 lbs./3000 $ft^2$, and that is sized at an addition rate of at least about 2.2 pounds/ton, is capable of running on the IBM Model 3800 high speed, continuous-forms laser printer without causing a rate of billowing in inches of increase per second×10,000 greater than about 5.

Further, the preferred paper according to the invention, that can be made into sheets of 8½×11 inch reprographic cut paper having a basis weight of about 15–24 lbs./1300 $ft^2$ and is sized at an addition rate of at least about 2.2 pounds/ton, is capable of running on a high speed laser printer or copier without causing misfeeds or jams at a rate of 5 or less in 10,000. The preferred paper according to the invention, having a basis weight of about 15–24 lbs./1300 $ft^2$, also can be converted to a standard perforated continuous form on the Hamilton-Stevens continuous form press at a press speed of at least about 1775 feet per minute.

The invention also comprises the process of converting the paper according to the invention to a standard perforated continuous form on a continuous forms press at a press speed of from about 1300 to 2000 feet per minute.

A further process according to the invention comprises running 8½×11 inch reprographic cut paper, having a basis weight of about 15–24 lbs./1300 $ft^2$, on a high speed, continuous laser printer or copier without causing misfeeds or jams at a rate of 5 or less in 10,000, preferably without causing misfeeds or jams at a rate of 1 or less in 10,000. By comparison, paper sized with standard AKD had a much higher rate of double feeds on the IBM 3825 high speed copier (14 double feeds in 14,250 sheets). In conventional copy-machine operation, 10 double feeds in 10,000 sheets is unacceptable. A machine manufacturer considers 1 double feed in 10,000 sheets to be unacceptable.

Another process according to the invention comprises converting the paper according to the invention into at least about 900 envelopes per minute, preferably at least about 1000 per minute.

DETAILED DESCRIPTION OF THE INVENTION

Alkaline sizing agents, that give levels of sizing comparable to those obtained with current AKD and ASA sizing technology, and improved handling performance in typical end-use and converting operations, have a reactive 2-oxetanone group and pendant hydrophobic hydrocarbon tails. In that respect, they resemble traditional AKD-based sizing agents, but unlike the saturated straight chains in the fatty acids used to prepare conventional solid alkyl ketene dimer based sizing agents, the hydrocarbon chain in one or both of the fatty acid chlorides used to prepare this class of sizing agents contain irregularities in the chemical structure of the pendant hydrocarbon chains, such as carbon-to-carbon double bonds and chain branching. Due to the irregularities in the pendant hydrocarbon chains, these sizing agents are not solid, and preferably are liquid, at or near room temperatures.

Examples of this class of sizing agents are 2-oxetanone based materials prepared from oleic acid, and 2-oxetanone based materials prepared from either Pamak-1 or Pamolyn 380 liquid fatty acid (fatty acid mixtures available from Hercules Incorporated and consisting primarily of oleic and linoleic acid. Other examples of fatty acids that may be used are the following unsaturated fatty acids: dodecenoic, tetradecenoic (myristoleic), hexadecenoic (palmitoleic), octadecadienoic (linolelaidic), octadecatrienoic (linolenic), eicosenoic (gadoleic), eicosatetraenoic (arachidonic), docosenoic (erucic), docosenoic (brassidic), and docosapentaenoic (clupanodonic) acids.

2-oxetanone multimers formed from mixtures of these fatty acids and a dicarboxylic acid are also examples, including: 2-oxetanone multimers prepared from a 2.5:1 mixture of oleic acid and sebacic acid, and 2-oxetanone multimers prepared from a 2.5:1 mixture of Pamak-1 fatty acid and azelaic acid. Preferred examples are 2-oxetanone multimers with fatty acid to diacid ratios ranging from 1:1 to 3.5:1. These reactive sizing agents are disclosed as being prepared using methods known from Japanese Kokai 168992/89, the disclosure of which is incorporated herein by reference. In the first step, acid chlorides from a mixture of fatty acid and dicarboxylic acid are formed, using phosphorous trichloride or another conventional chlorination agent. The acid chlorides are then dehydrochlorinated in the presence of triethylamine or another suitable base, to form the multimer mixture. Stable emulsions of these sizing agents can be prepared in the same way as standard AKD emulsions.

Experimental Procedures

Paper for evaluation on the IBM 3800 was prepared on the pilot paper machine at Western Michigan University.

To make a typical forms bond paper-making stock, the pulp furnish (three parts Southern hardwood kraft pulp and one part Southern softwood kraft pulp) was refined to 425 ml Canadian Standard Freeness (C.S.F.) using a double disk refiner. Prior to the addition of the filler to the pulp furnish (10% medium particle-size precipitated calcium carbonate), the pH (7.8–8.0), alkalinity (150–200 p.p.m.), and hardness (100 p.p.m.) of the paper making stock were adjusted using the appropriate amounts of $NaHCO_3$, NaOH, and $CaCl_2$.

The 2-oxetanone sizing agents, including the multimers, were prepared by methods and used conventionally to prepare commercial AKD's; i.e., acid chlorides from a mixture of fatty acid and dicarboxylic acid are formed, using a conventional chlorination agent, and the acid chlorides are dehydrochlorinated in the presence of a suitable base. The 2-oxetanone sizing agent emulsions, including the multimer emulsions, were prepared according to the disclosure of U.S. Pat. No. 4,317,756, which is incorporated herein by reference, with particular reference to Example 5 of the patent. Wet-end additions of sizing agent, quaternary-amine-substituted cationic starch (0.75%), alum (0.2%), and retention aid (0.025%) were made. Stock temperature at the headbox and white water tray was controlled at 110° F.

The wet process were set at 40 p.s.i. guage. A dryer profile that gave 1–2% moisture at the size press and 4–6% moisture at the reel was used (77 f.p.m.). Before the size press, the sizing level was measured on a sample of paper torn from the edge of the sheet, using the Hercules Size Test (HST). With Hercules Test Ink #2, the reflectance was 80%. Approximately 35 lb/ton of an oxidized corn starch and 1 lb/ton of NaCl were added at the size press (130° F., pH 8). Calender pressure and reel moisture were adjusted to obtain a Sheffield smoothness of 150 flow units at the reel (Column #2, felt side up).

A 35 minute roll of paper from each paper making condition was collected and converted on a commercial forms press to two boxes of standard 8½"×11" forms. Samples were also collected before and after each 35 minute roll for natural aged size testing, basis weight (46 #/3000 $ft^2$), and smoothness testing.

The converted paper was allowed to equilibrate in the printer room for at least one day prior to evaluation. Each box of paper allowed a 10–14 minute (220 f.p.m.) evaluation on the IBM 3800. All samples were tested in duplicate. A standard acid fine paper was run for at least two minutes between each evaluation to reestablish initial machine conditions.

The height of billowing in inches at the end of the run, and the rate at which billowing occurred (inches of increase in billowing per second), were used to measure the effectiveness of each approach.

EXAMPLE 1

A number of sizing agents were tested for their effects on the IBM 3800 runnability of a difficult-to-convert grade of alkaline fine paper. The above Experimental Procedures were followed.

The rate of paper billowing on an IBM 3800 high speed printer was used to evaluate the converting performance of each sample of paper. A summary of the results of this testing is given in Table 1.

Several 2-oxetanone based alkaline sizing agents are shown that give a better balance of sizing and runnability on the IBM 3800 (for instance, less billowing at similar levels of sizing) than a standard AKD sizing agent made for comparative purposes. The standard AKD sizing agent was made from a mixture of stearic and palmitic acids. This is a standard sizing agent of the type that lacks any irregularities, such as double bonds or branching, in its pendant hydrocarbon chains. The best balance of sizing and handling performance was obtained with one of the following agents: a 2-oxetanone based sizing material made from a mixture of about 73% oleic acid, about 8% linoleic acid, and about 7% palmitoleic acid, the remainder being a mixture of saturated and unsaturated fatty acids, available from Henkel-Emery under the name Emersol NF (referred to herein for convenience along with similar sizes based on oleic acid as an oleic acid size).

Another 2-oxetanone size prepared from Pamolyn 380 fatty acid, consisting primarily of oleic and linoleic acid and available from Hercules Incorporated, and a 2-oxetanone sizing agent made from isostearic acid. All these sizing agents were liquids at 25° C., and in particular, at equal sizing levels, gave better converting performance on the IBM 3800 than the control made from a mixture of stearic and palmitic acids.

TABLE 1

| Composition of Size | Addition Level | Natural Aged HST | Rate of Billowing* |
|---|---|---|---|
| Oleic Acid | 1.5 | 122 | 1.6 |
| " | 2.2 | 212 | 15.1 |
| " | 3.0 | 265 | 29.4 |
| " | 4.0 | 331 | 55.5 |
| Oleic Acid (Pamolyn 380) | 2.2 | 62 | 1.6 |

TABLE 1-continued

| Composition of Size | Addition Level | Natural Aged HST | Rate of Billowing* |
|---|---|---|---|
| Isostearic | 2.2 | 176 | 1.5 |
| Control | 1.5 | 162 | 23.8 |
| " | 2.2 | 320 | 55.0 |

*Inches of billowing/sec. × 10,000.

EXAMPLE 2

Additional sizing agents were tested for their effects on IBM 3800 paper runnability in a second set of experiments. The above Experimental Procedures were followed.

An AKD emulsion and an alkenyl succinic anhydride (ASA) emulsion were evaluated as controls. The ASA emulsion was prepared as described by Farley and Wasser in "The Sizing of Paper (Second Edition)," "Sizing with Alkenyl Succinic Anhydride" page 51, (1991). The performing parameters measured in these studies were natural aged sizing and runnability on the IBM 3800. A summary of the results of these evaluations is given in Table 2.

The materials tested gave a better balance of sizing and converting performance (less billowing at the same level of sizing) than either of the commercial ASA or AKD sizing agents used as controls. The best balance of sizing and handling performance was obtained with: a 2-oxetanone size prepared from Pamak-1 fatty acid (a mixture comprised primarily of oleic and linoleic acid) and a 2-oxetanone multimer prepared from a 2.5:1 mixture of oleic acid and sebacic acid. Both sizing agents gave levels of sizing comparable to that obtained with the ASA and AKD controls. Both sizing agents gave paper with better runnability on the IBM 3800 than the paper sized with either the ASA or AKD standards.

TABLE 2

| Composition of Size | Addition Rate | Natural Aged HST | Rate of Billowing |
|---|---|---|---|
| Oleic/ Linoleic | 1.5 | 34 | <1.7 |
| Oleic/ Linoleic | 2.2 | 203 | <1.7 |
| Oleic/ Linoleic | 3.0 | 193 | <4.6 |
| Oleic/ Linoleic | 4.0 | 250 | 17.5 |
| Oleic/ Sebacic | 1.5 | 53 | <10.4 |
| Oleic/ Sebacic | 2.2 | 178 | <1.7 |
| Oleic/ Sebacic | 3.0 | 270 | <3.4 |
| Oleic/ Sebacic | 4.0 | 315 | 16.6 |
| Control (AKD) | 1.5 | 162 | 166 |
| Control (AKD) | 2.2 | 320 | 48 |
| Control (ASA) | 1.5 | 127 | 52 |
| Control (ASA) | 2.2 | 236 | 83 |
| Control (ASA) | 3.0 | 286 | 166 |

EXAMPLE 3

Two 2-oxetanone multimers prepared from mixtures of azelaic acid and oleic acid, and mixtures of azelaic acid and oleic/linoleic fatty acid, were tested. Paper for testing was prepared on the pilot paper machine using the conditions described in the Experimental Procedures. A standard paper sized with a commercial AKD size dispersion was evaluated as a control. A summary of the results of these evaluations is given in Table 3.

Both types of 2-oxetanone multimer gave levels of HST sizing similar to those obtained with the standard AKD control. Both multimer sizes gave lower levels of billowing on the IBM 3800 than the control.

TABLE 3

| Composition of Size | Addition Level | Natural Aged HST | Rate of Billowing |
|---|---|---|---|
| Oleic/ Azeleic 2.5:1 | 2.2 | 186 | <1.2 |
| Oleic/ Azeleic 2.5:1 | 3 | 301 | <2.2 |
| Oleic/ Azeleic 2.5:1 | 4 | 347 | <2.3 |
| Oleic/ Linoleic: Azeleic 2.5:1 | 2.2 | 160 | <2.4 |
| Oleic/ Linoleic: Azeleic 2.5:1 | 3 | 254 | <2.4 |
| Oleic/ Linoleic: Azeleic 2.5:1 | 4 | 287 | <2.4 |
| Control | 2.2 | 267 | 10 |
| " | 3 | 359 | 23 |

EXAMPLE 4

A series of Pamak-1 fatty acid:azelaic acid 2-oxetanone multimers with fatty acid to dicarboxylic acid ratios ranging from 1.5:1 to 3.5:1 were evaluated in a fourth set of experiments. Paper for testing was again prepared on the pilot paper machine at Western Michigan University using the conditions described in Example 1. The performance parameters measured in these studies were: natural aged sizing efficiency (acid ink) and runnability on the IBM 3800. Standard AKD and ASA sized paper were evaluated as controls. A summary of the results of these evaluations is given in Table 4.

All of the Pamak-1:azelaic acid 2-oxetanone multimers gave a better balance of sizing and IBM 3800 runnability than either of the commercial controls.

TABLE 4

| Composition of Size | Addition Level | Natural Aged HST | Rate of Billowing |
|---|---|---|---|
| 1.5:1 | 2.5 | 209 | <5 |
| " | 4.5 | 339 | <5 |
| 2.5:1 | 2.0 | 214 | <5 |
| " | 3.5 | 312 | <5 |
| " | 4.0 | 303 | <5 |
| 3.5:1 | 2.5 | 312 | <5 |
| " | 4.0 | 303 | <5 |
| Control (AKD) | 1.5 | 255 | <5 |

TABLE 4-continued

| Composition of Size | Addition Level | Natural Aged HST | Rate of Billowing |
|---|---|---|---|
| Control (AKD) | 3.0 | 359 | 15 |
| Control (ASA) | 3.0 | 253 | 23 |

EXAMPLE 5

An evaluation of a 2-oxetanone size made for oleic acid, with a comparison to a AKD commercial size made from a mixture of palmitic and stearic acids, was carried out on a high speed commercial fine paper machine (3000 f.p.m., 20 tons of paper produced per hour, 15 lb/1300 $ft^2$). A typical forms bond paper making stock similar to that used in Example 1 was used. Addition levels of the two sizing agents were adjusted to give comparable levels of HST sizing (20–30 seconds, 85% reflectance, Hercules Test Ink #2). No deposits were observed on the paper machine.

The paper produced under these conditions was then evaluated on a high speed Hamilton continuous forms press. The Hamilton press converts paper to a standard perforated continuous form. Press speed was used as a measure of performance. Two samples of the AKD control were tested before and after the evaluation of the paper sized with the oleic acid based size. The results are shown in Table 5. The paper sized with the oleic acid size clearly converted at a significantly higher press speed than the paper sized with the AKD control.

TABLE 5

| Run # | Sizing Agent | Hamilton Press Speed |
|---|---|---|
| 1 | AKD CONTROL | 1740 f.p.m. |
| 2 | AKD CONTROL | 1740 f.p.m. |
| 3 | OLEIC ACID 2-OXETANONE | 1800 f.p.m. |
| 4 | OLEIC ACID 2-OXETANONE | 1775 f.p.m. |
| 5 | AKD CONTROL | 1730 f.p.m. |
| 6 | AKD CONTROL | 1725 f.p.m. |

EXAMPLE 6

An evaluation of oleic acid 2-oxetanone size, with a comparison with an AKD commercial standard size prepared from a mixture of palmitic and stearic acid, was carried out on a commercial paper machine producing a xerographic grade of paper (3100 f.p.m., 42 lb/3000 $ft^2$). As in Example 5, addition levels of each sizing agent were adjusted to give comparable levels of HST sizing after natural aging (100–200 seconds of HST sizing, 80% reflectance, Hercules Test Ink #2). No deposits were observed on the paper machine. The paper produced with oleic acid 2-oxetanone size ran without any jams or double feeds on a high speed IBM 3825 sheet fed copier (no double feeds in 14,250 sheets). Paper prepared with the AKD controls had a much higher rate of double feeds on the IBM 3825 (14 double feeds in 14,250 sheets).

EXAMPLE 7

A 2-oxetanone size was prepared from oleic acid by known methods. A sizing emulsion was then prepared from the oleic acid-based size by known methods. Copy paper sized with the oleic acid-based sizing emulsion was made on a commercial fine paper machine (3100 f.p.m., 40 tons of paper produced per hour, 20#/1300 $ft^2$, 10% precipitated calcium carbonate, 1# of sodium chloride/ton of paper added at the size press). Copy paper sized with a standard AKD (prepared from a mixture of palmitic acid and stearic acid) sizing emulsion was also made as a control. The addition level of each sizing agent was adjusted to give 50–100 seconds of HST sizing (1.4# of standard commercial AKD, 1.9–2.1# of oleic acid size per ton of paper, 80% reflectance, Hercules Test Ink #2).

The copy paper sized with oleic acid size ran without any jams or double feeds on a high speed IBM 3825 sheet fed copier (no double feeds in 99,000 sheets). The paper sized with the AKD control had a much high rate of double feeds on the IBM 3825 (14 double feeds in 27,000 sheets).

EXAMPLE 8

Two samples of 2-oxetanone-based sizing agents were prepared from oleic acid and Pamak-1 fatty acid (a mixture consisting primarily of linoleic and oleic acid) by known methods. Sizing emulsions were prepared from both sizes. Forms bond paper samples sized respectively with the Pamak-1 fatty acid-based size and the oleic acid-based size were made on a commercial fine paper machine (approximately 3000 f.p.m., 16 lb/1300 $ft^2$, 5 lb/ton alum, 10 lb/ton quaternary amine substituted starch). Forms bond paper sized with a commercial AKD (prepared from a mixture of palmitic acid and stearic acid) sizing emulsion was also made as a control. The addition level of each sizing agent (See Table 6) was adjusted to give comparable levels of HST sizing at the reel (70% reflectance, Hercules Tesk Ink #2).

The paper produced under these conditions was converted on a high speed Hamilton continuous forms press. The Hamilton press converts paper to a standard perforated continuous form. Press speed was used as a measure of paper performance. The results are listed in the following Table 6. Each press speed is an average of measurements made on six different rolls of paper. The paper sized with the oleic acid-based size and the paper sized with the Pamak-1 fatty acid-based size converted at a significantly higher press speed than the paper sized with the AKD control.

TABLE 6

| Run # | Sizing Agent | Add'n Level | HST Sizing (seconds) | Hamilton Press Speed |
|---|---|---|---|---|
| 1 | AKD Control | 2.0#/Ton | 208 | 1857 f.p.m. |
| 2 | Oleic Acid-based Size | 2.5#/Ton | 183 | 1957 f.p.m. |
| 3 | PAMAK-1 Fatty Acid-based Size | 2.5#/Ton | 185 | 1985 f.p.m. |

EXAMPLE 9

A 2-oxetanone-based sizing agent was prepared from oleic acid by known methods. A sizing emulsion was then prepared from the oleic acid-based sizing agent by known methods. Envelope paper sized with the oleic acid-based sizing emulsion and containing 16% precipitated calcium carbonate was made on a commercial fine paper machine in two basis weights, 20 lb and 24 lb per 1300 $ft^2$. Envelope paper sized with a standard commercial AKD (prepared from a mixture of palmitic acid and stearic acid) and a commercial surface sizing agent (0.5 lb/ton Graphsize A) sizing emulsion was also made as a control. The addition level of each internal sizing agent was adjusted to give comparable levels of HST sizing at the reel (100–150 seconds, 80% reflectance, Hercules Test Ink #2).

The paper sized with each of the two sizing agents was converted to envelopes on a Winkler & Dunnebier CH envelope folder. The 20 lb paper was converted to "Church" envelopes. The 24 lb paper was converted to standard #10 envelopes. Envelope production rate (envelopes per minute) was used as a measure of paper converting performance. The results are listed in the following Table 7. The paper sized with the oleic acid-based size converted at a significantly higher speed than the paper sized with the AKD control.

TABLE 7

| Sizing Agent | Size Add'n Level | HST (sec.) | Basis Weight | Product | Envelopes per Minute |
|---|---|---|---|---|---|
| AKD Control | 2.0#/Ton | 100–150 | 20# | Church Envelope | 850 |
| Oleic Acid-based Size | 2.9#/Ton | 100–150 | 20# | Church Envelope | 900–950 |
| AKD Control | 1.5#/Ton | 100–150 | 24# | #10 Envelope | 965 |
| Oleic Acid-based Size | 2.5#/Ton | 100–150 | 24# | #10 Envelope | 1000–1015 |

We claim:

1. A sizing agent consisting of a 2-oxetanone having pendent hydrocarbyl tails wherein the hydrocarbyl tails are branched alkyl.

2. A sizing agent as claimed in claim 1, in which the hydrocarbyl tails have six or more carbon atoms each.

3. A sizing agent as claimed in claim 1, in which the hydrocarbyl tails have 10–22 carbon atoms each.

4. A sizing agent as claimed in claim 3, in which the 2-oxetanone] is liquid at 25° C.

5. A sizing agent as claimed in claim 3, wherein the branched hydrocarbyl tails are each derived from isostearic acid.

6. A sizing agent as claimed in claim 1, in which the 2-oxetanone is not solid at 25° C.

7. A sizing agent as claimed in claim 1, in which the 2-oxetanone is liquid at 25° C.

8. A sizing agent as claimed in claim 1, wherein the 2-oxetanone has a single 2-oxetanone ring.

9. A sizing agent as claimed in claim 8, wherein the branched hydrocarbyl tails are each derived from isostearic acid.

10. A sizing agent as claimed in claim 1, wherein the 2-oxetanone is a 2-oxetanone multimer.

11. A sizing agent as claimed in claim 1, wherein the branched hydrocarbyl tails to each derived from isostearic acid.

12. A sizing agent as claimed in claim 11, wherein the 2-oxetanone sizing agent is a 2-oxetanone multimer formed from a mixture comprising isostearic acid and dicarboxylic acid.

13. Paper made under alkaline conditions and sized with the sizing agent of claim 1.

14. Paper as claimed in claim 13 in the form of continuous forms bond paper.

15. Paper as claimed in claim 13 in the form of adding machine paper.

16. Paper as claimed in claim 13 in the form of envelope-making paper.

17. Paper as claimed in claim 13 in the form of an envelope.

18. An emulsion comprising the sizing agent of claim 1.

19. A sizing agent consisting of a 2-oxetanone of the formula

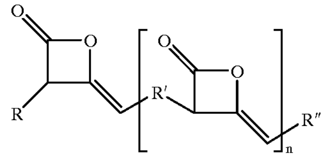

in which n is 0–6, R and R" are each branched alkyl; and R' is alkylene.

20. The sizing agent as claimed in claim 19 wherein n is 0.

21. The sizing agent as claimed in claim 20 in which the 2-oxetanone sizing agent is a liquid at 25° C.

22. The sizing agent as claimed in claim 20 where R and R'" are each derived from isostearic acid.

23. The sizing agent as claimed in claim 20 wherein R and R" have 10–22 carbon atoms.

24. The sizing agent as claimed in claim 23 wherein R' is $C_6$–$C_{16}$ straight chain alkyl.

25. The sizing agent as claimed in claim 19 wherein n is greater than 0.

26. The sizing agent as claimed in claim 19 in which the 2-oxetanone sizing agent is not solid at 25° C.

27. The sizing agent as claimed in claim 19 in which the 2-oxetanone sizing agent is a liquid at 25° C.

28. The sizing agent as claimed in claim 19 wherein R and R" have 10–22 carbon atoms.

29. The sizing agent as claimed in claim 19 wherein R' is $C_6$–$C_{16}$ straight chain alkyl.

30. Paper made under alkaline conditions and sized with the sizing agent of claim 19.

31. An emulsion comprising the sizing agent of claim 19.

* * * * *